United States Patent [19]

Byrum

[11] Plant 3,990

[45] Dec. 14, 1976

[54] ROSE PLANT SEEDLING NO. 71-86L

[75] Inventor: Roy L. Byrum, Richmond, Ind.

[73] Assignee: Joseph H. Hill Company, Richmond, Ind.

[21] Appl. No.: 651,203

[22] Filed: Jan. 21, 1976

[51] Int. Cl.[2] ..... A01H 5/00

[52] U.S. Cl. ..... Plt./22

[58] Field of Search ..... Plt./22, 26–27

*Primary Examiner*—Robert E. Bagwill

*Attorney, Agent, or Firm*—Charles W. Rummler

[57] ABSTRACT

A new variety of rose plant developed for commercial greenhouse culture and the commercial production of cut flowers, particularly distinguished by its abundant year around production of medium large flowers having an unusual lavender color and a strong tea fragrance. This new plant is a floribunda having a free and vigorous growth habit, one to three buds being borne on a strong stem of medium length which may be commercially disbudded to present a single blossom having a strong, erect peduncle of medium length.

1 Drawing Figure

BACKGROUND OF THE NEW PLANT

My new variety of rose plant is a cross of Sterling Silver (U.S. Plant Pat. No. 1,433) with an unnamed seedling, identified in my breeding records as No. 63-10L, as the pollen parent. The cross resulting in this plant was made by me at Richmond, Indiana, in the Spring of 1970 with the object of creating a floribunda variety that would have the fragrance and good color of its hybrid tea seed parent and yet have improved vigor and greater flower production throughout the entire year. This seedling produced its first flower in the Fall of 1971 and was observed to have the characteristics which I sought as well as a very unusual coloring and was therefore selected for propagation and test. Reproduction was done under my direction by budding and succeeding reproductions, by budding, at Richmond, Indiana, and Hamilton City, California, have demonstrated that the distinguishing characteristics of this new variety are firmly fixed and hold true.

DESCRIPTION OF THE DRAWING

My new variety of rose plant is illustrated by the accompanying full color photographic drawing which shows the form and color of the newly opened and mature blossoms, specimens of buds, a specimen of young growth of wood and foliage, and top and under side views of typical leaves, the colors shown being as nearly true as can be reasonably expected from conventional photographic procedures.

DESCRIPTION OF THE NEW PLANT

The following is a description, in detail, of my new variety of rose plant, with color designations according to Koster's Color Guide (K) and the Horticultural Colour Chart (HCC) by Robert F. Wilson as published by the Royal Horticultural Society at London, England, the following data being from observations of greenhouse plants grown at Richmond, Indiana.

THE PLANT

Origin: Seedling.

Parentage:

*Seed parent.*—Sterling Silver (PP 1433).

*Pollen parent.*—Unnamed and unpatented. Seedling No. 63-10L.

Classification:

*Botanical.*—Hybrid rose.

*Commercial.*—Floribunda.

Form: Bush.

Habit: Upright and much branched.

Growth: Free and vigorous.

Canes: Straight, strong and of medium diameter and length.

*Main Stems.*—Color—Spinach Green 0960/2 (HCC). Thorns—Few, straight and of medium length with a short, broad base. Color—Lilac, Plate No. 48 (K). Prickles—Few. Color—Lilac, Plate No. 48 (K). Hairs—None.

*Branches.*—Color—Spinach Green 0960/1 (HCC). Thorns—Few, straight and short with a short, narrow base. Color—Sap Green 62/3 (HCC) the base being tinted with Solferino Purple 26/3 (HCC). Prickles and Hairs—None.

*New Shoots.*—Color—Oxblood Red 00823/2 (HCC) shaded with Spinach Green 0960/2 (HCC). Thorns—Few, straight and of medium length with a short, narrow base. Color—Indian Lake 826/2 (HCC) with Sap Green 62/3 (HCC) at the tip. Prickles—Few. Color—Indian Lake 826/2 (HCC) with Sap Green 62/3 (HCC) at the tip. Hairs—None.

Foliage: Quantity—Abundant.

*Leaves.*—Large and odd pinnate in shape.

*Leaflets.*—3 to 7 in number.

*Shape.*—Ovoid, with an acute apex, round base and a simply serrate margin.

*Texture.*—Moderately heavy.

*Aspect.*—Glossy.

*Color.*—Mature Leaf: Upper Surface—Nearest color Spinach Green 0960/2 (HCC). Under Surface—Cedar Green, Plate No. 80 (K). Young Leaf: Upper Surface—Oxblood Red 00823/2 (HCC) shaded with Spinach Green 0960/1 (HCC). Under Surface—Garnet Brown 00918/2 (HCC).

*Rachis.*—Heavy, with smooth, grooved upper side and moderately prickly under side.

*Stipules.*—Medium in length and width with short points and turning outward at an angle less than 45° from the rachis.

THE BUD

Before the calyx breaks:

*Size.*—Medium small.

*Form.*—Short pointed, with a conspicuous neck and foliaceous appendages on the surface of the bud which have slender parts extending beyond the bud tip for a distance of about ¼ or more of the bud length.

*Color of Calyx.*—Scheeles Green 860/3 (HCC).

As calyx breaks:

*Color.*—Erythrite Red 0027 (HCC).

As first petal opens:

*Bud size.*—Medium large.

*Form.*—Short pointed.

*Color of Petals.*—Outside—Nearest color Magenta, Plate No. 50 (K). Inside—Upper portion Lilac Purple 031/1 (HCC) with base of Empire Yellow 603/3 (HCC).

*Sepals.*—Permanent, of medium length and generally straight. Color: Inside—Scheeles Green 860/3 (HCC) overlaid with white fuzz. Outside—Scheeles Green 860/2 (HCC).

Bud Opening: The bud opens up well in greenhouse.

Peduncle: Strong, erect and of medium length and diameter.

*Bark.*—Almost smooth.

*Color.*—Scheeles Green 860/3 (HCC).

*Thorns and Prickles.*—None.

*Hairs.*—Few. Color—Pure White, Plate No. 1 (K).

THE FLOWER

Blooming Habit: Abundant and continuous.

Size: Medium large—3 to 4 inches in diameter when fully opened.

Borne: One to three to a stem—disbudded commercially to a single flower—on strong stems of medium length.

Shape: Full and high centered, at first, with petals very tightly rolled outward; becoming open with petals very loosely rolled outward at maturity.

Petalage: Double, with 25 to 30 petals regularly arranged.

*Shape of Petals.*—Ovate with mucronate apex, intermediate petals having one notch and inside petals having one or two notches.

*Texture.*—Moderately thick.

*Aspect.*—Velvety on inside and outside surfaces.

COLOR OF PETALS

A. The following description is from a flower newly opened in August 1975.

Outside Petals

Outside Surface: Amaranth Rose 530 (HCC) with a base of Empire Yellow 603/1 (HCC).

Inside Surface: Roseine Purple 629/2 (HCC) with a base of Empire Yellow 603/1 (HCC).

Intermediate Petals

Outside Surface: Amaranth Rose 530 (HCC) with base of Empire Yellow 603/3 (HCC).

Inside Surface: Roseine Purple 629/2 (HCC) with base of Empire Yellow 603/1 (HCC).

Inner Petals

Outside Surface: Amaranth Rose 530 (HCC) with base of Empire Yellow 603/3 (HCC).

Inside Surface: Roseine Purple 629/2 (HCC) with base of Empire Yellow 603/2 (HCC).

B. The following data is from observations of a flower opened for three days in September 1975.

Outside Petals

Outside Surface: Amaranth Rose 530/1 (HCC) with Primrose Yellow 601/3 (HCC) at the base.

Inside Surface: Mallow Purple 630/2 (HCC) with Primrose Yellow 601/2 at the base.

Intermediate Petals

Outside Surface: Amaranth Rose 530/2 (HCC) with Primrose Yellow 601/3 (HCC) at the base.

Inside Surface: Amaranth Rose 530/1 (HCC) with Primrose Yellow 601/2 (HCC) at the base.

Inner Petals

Outside Surface: Amaranth Rose 530/2 (HCC) with Primrose Yellow 601/3 (HCC) at the base.

Inside Surface: Mallow Purple 630/3 (HCC) with Primrose Yellow 601/2 (HCC) at the base.

General Color Effect of Open Bloom:

*Newly Opened Flower.*—Roseine Purple 629/2 (HCC).

*Three Days Open Flower.*—Amaranth Rose 530/1 (HCC).

Persistence: Flower petals hang on and dry.

Fragrance: Strong tea.

Flower Longevity: 5 to 7 days at living room temperatures in August.

REPRODUCTIVE ORGANS

Stamens: Many in number, regularly arranged about the pistils.

*Filaments.*—Of Medium length, many with anthers.

*Color.*—Barium Yellow 503 (HCC).

*Anthers.*—Medium in size. All open at once.

*Color.*—Primrose Yellow 601/2 (HCC) overlaid with Apricot 609/2 (HCC).

*Pollen.*—Abundant.

*Color.*—Cadmium Orange 8/1 (HCC).

Pistils: Medium in number.

*Styles.*—Uneven and of medium length, moderately thin and bunched.

*Color.*—Pure White, Plate No. 1 (K).

*Color of Stigmas.*—Pure White, Plate No. 1 (K).

Ovularies: All encased in calyx.

Hips and Seeds: None.

My new variety of rose plant is superior to its seed parent, Sterling Silver, because it is a floribunda, whereas the seed parent is a hybrid tea rose. This new plant produces considerably more flowers throughout the entire year and is a distinct novelty because of its lavender flower color and strong fragrance. The new plant bushes more profusely than either of its parents and through this cross has more vigor and increased production.

The new plant most nearly resembles Angel Face (U.S. Plant Pat. No. 2,792) in color but has the advantage of forcing well all year without being affected by short days and cloudy weather. Because of the unusual lavender color and strong aroma of its flowers, this new plant is a distinct departure from the ordinary standards of most modern floribunda varieties.

I claim:

1. A new and distinct variety of rose plant substantially as herein shown and described, characterized by the lavender coloration and strong fragrance of its blooms, which are borne on strong stems of medium length, and by its abundant year around production of flowers of medium large size.

* * * * *

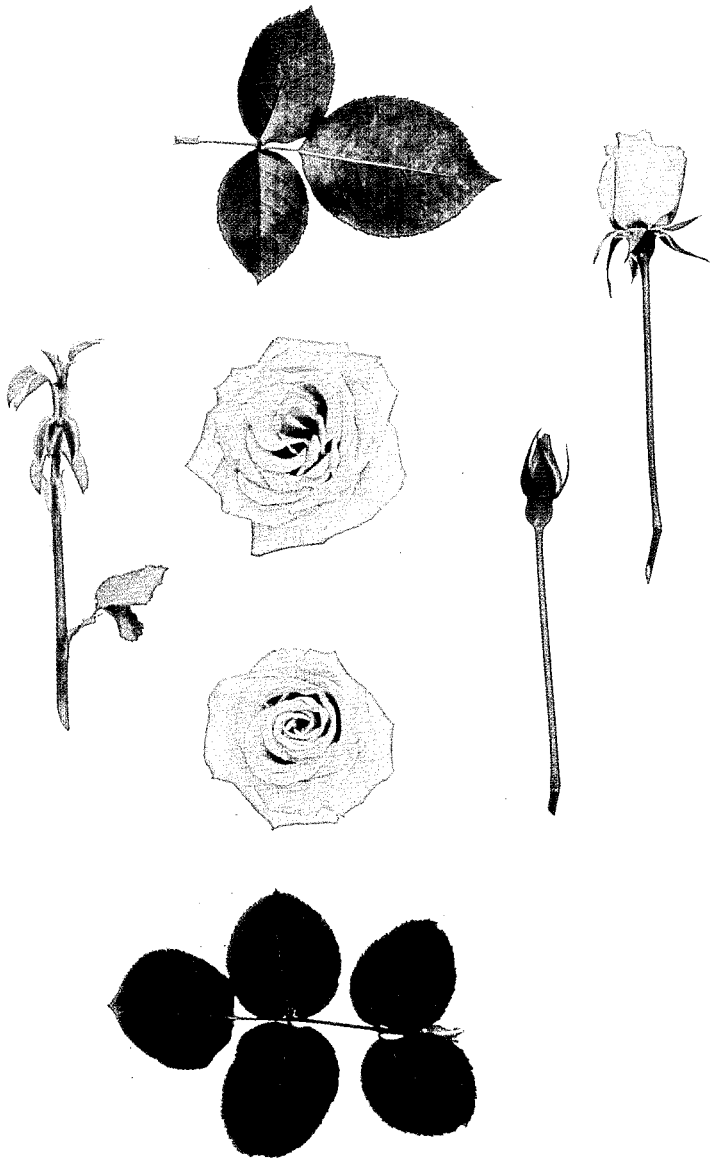

Dec. 14, 1976 R. L. BYRUM Plant Pat. 3,990
ROSE PLANT SEEDLING NO.
71-86L
Filed Jan. 21, 1976